(12) United States Patent
Schulte

(10) Patent No.: US 6,780,149 B1
(45) Date of Patent: Aug. 24, 2004

(54) PATIENT MOTION MONITORING SYSTEM FOR PROTON THERAPY

(75) Inventor: Reinhard Schulte, Grand Terrace, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

(21) Appl. No.: 09/958,457

(22) PCT Filed: Apr. 7, 2000

(86) PCT No.: PCT/US00/09444

§ 371 (c)(1),
(2), (4) Date: May 13, 2002

(87) PCT Pub. No.: WO00/59575

PCT Pub. Date: Oct. 12, 2000

(51) Int. Cl.[7] .............................. A61N 5/00; A61B 6/03
(52) U.S. Cl. ........................................... 600/1; 600/426
(58) Field of Search ........................... 600/1, 409, 426, 600/427, 429, 439, 424, 478, 414, 410; 606/130; 378/69, 162, 204, 205, 207, 208; 356/141.1, 623, 624; 433/27, 68, 213; 250/227.11, 231.19, 206.1, 227.23, 251, 492.1

(56) References Cited

U.S. PATENT DOCUMENTS

| | | | |
|---|---|---|---|
| 4,378,813 A | | 4/1983 | Feldstein et al. |
| 4,666,304 A | * | 5/1987 | Davies .......................... 356/624 |
| 4,711,578 A | * | 12/1987 | Chaimowicz ................ 356/624 |
| 4,815,448 A | | 3/1989 | Mills |
| 4,848,340 A | | 7/1989 | Bille et al. |
| 5,037,374 A | | 8/1991 | Carol |
| 5,049,147 A | | 9/1991 | Danon |
| 5,279,309 A | | 1/1994 | Taylor et al. |
| 5,446,548 A | | 8/1995 | Gerig et al. |
| 5,485,833 A | | 1/1996 | Dietz |
| 5,538,494 A | | 7/1996 | Matsuda |
| 5,588,430 A | * | 12/1996 | Bova et al. .................. 600/429 |
| 5,622,170 A | * | 4/1997 | Schulz ........................ 600/424 |
| 5,630,422 A | | 5/1997 | Zanakis |
| 5,676,673 A | | 10/1997 | Ferre et al. |
| 5,755,725 A | | 5/1998 | Druais |
| 5,782,842 A | | 7/1998 | Kloess et al. |
| 5,800,352 A | | 9/1998 | Ferre et al. |
| 5,865,832 A | | 2/1999 | Knopp et al. |
| 5,866,912 A | * | 2/1999 | Slater et al. .............. 250/492.1 |
| 6,144,875 A | * | 11/2000 | Schweikard et al. ........ 600/427 |
| 6,405,072 B1 | * | 6/2002 | Cosman ....................... 600/426 |
| 6,419,680 B1 | * | 7/2002 | Cosman et al. .............. 606/130 |

* cited by examiner

Primary Examiner—Mary Beth Jones
Assistant Examiner—Nikita R Veniaminov
(74) Attorney, Agent, or Firm—Knobbe, Martens, Olson & Bear, LLP

(57) ABSTRACT

A patient motion monitoring system (102) for use in a proton therapy center (100) is disclosed. The patient monitoring system (102) includes a plurality of position detector assemblies (162) with each position detector assembly (162) being constructed of a flexibly rigid support arm (132) attached to a position sensor (130). Each support arm (132) of the plurality of position detector assemblies (162) is detachably mounted to a supporting structure so as to allow the corresponding position sensor (130) to be positioned adjacent a patient (104) who is receiving proton therapy. Furthermore, each position sensor (130) of the plurality of position detector assemblies (162) generates a position signal that is indicative of the distance between a front surface of the position sensor, and an adjacent surface of the patient. The patient motion monitoring system (102) further includes a controller (160) which is adapted to receive each position signal from the plurality of position detector assemblies (162), a display (144), and an alarm (148) to indicate if a patient has moved out of position.

47 Claims, 7 Drawing Sheets

PATIENT MOTION MONITORING SYSTEM FOR PROTON THERAPY

BACKGROUND OF THE INVENTION

1. Field of the Invention

The present invention relates to patient motion monitoring systems used in medical radiation facilities, and in particular, patient motion monitoring systems that are adapted to prevent a collimated beam of particles from reaching a patient whenever the patient moves more than a threshold level.

2. Description of the Related Art

Energetic particle beams are sometimes used by medical practitioners to treat cancerous regions in patients. In particular, when a particle beam is directed at a cancerous tumor within a patient, the penetrating nature of the particle beam allows the beam to reach a deep seated tumor and deposit energy within the tumor. As energy is absorbed by the tumor, the DNA structures within the cells of the tumor are altered. If enough energy is absorbed by the tumor, it is possible to cause irreparable damage to the DNA structures, thus causing the tumor to diminish in size or even die completely.

A particularly effective form of particle beam therapy involves the use of energetic protons. In particular, proton therapy centers, such as the Loma Linda Proton Facility at Loma Linda University in Loma Linda. Calif., are capable of producing a proton beam having a per particle energy up to 256 MeV. Protons within this energy range are able to penetrate deeply into the human body in a substantially straight path and deposit the majority of their energy in a localized region of the body. In particular, if the energy of a proton is sufficiently above a threshold value, known as the "Bragg peak", then the proton loses kinetic energy at a moderate rate as it passes through matter. However, when the kinetic energy of the proton is reduced to the Bragg peak threshold, the remaining kinetic energy of the proton is rapidly released. Therefore, a proton beam can be configured to release the majority of its energy within a tumor of a patient by adjusting the energy of the proton beam according to the amount of cellular material that is situated in front of the tumor so that the proton energy is reduced to the Bragg peak as the proton reaches the tumor.

However, given the relatively high radiobiologic effects of particle beams, such as proton beams, it is often desirable to limit patient movement during treatment so that movement of the patient will not result in the beam being misdirected and affecting healthy tissue within the patient's body. To prevent misalignment between the proton beam and the tumor in proton therapy, stereotactic fixation systems such as those described in U.S. Pat. Nos. 5,797,924, 5,549,616, and 5,464,411 have been developed and are often used in the treatment process. In particular, these immobilization devices are designed to limit the range of motion of the patient to within a fixed tolerance which is suitable for treating comparatively large tumors.

However, as treatment of smaller tumors located in more sensitive regions has become more desirable, an increasing need has developed for systems capable of preventing excessive misalignment. For example, a new field of proton therapy is being investigated which focuses on small intracranial tumors and functional disorders of the brain. In these cases the proton beam is required to align with relatively small intracranial targets with diameters between 1 cm and 3 cm. Given that tumors are surrounded by brain tissue misalignment of the beam in this environment can be very harmful to the patient. Consequently, correct patient alignment within 1 mm is an indispensable requirement for these treatments.

In research studies performed by the Applicants, the movement of patients receiving proton beam therapy while utilizing prior art stereotactic fixation immobilization devices was monitored. In particular, the results of these studies indicate that patient movement by as much as several mm. Furthermore, these studies indicate that patient motion is often oscillatory in nature with an average patient position that is within 1 mm of the ideal position and a period that often correlates to respiratory activity. Therefore, it is apparent from these results that the use of immobilization devices known in the art are not sufficient to provide optimal treatment of small intracranial targets with diameters between 1 cm and 3 cm.

From the foregoing, it will be appreciated that there is a need for a patient monitoring system that operates in conjunction with a proton beam facility that is capable of detecting movement of a patient by as little as 1 mm in any direction furthermore, this system should be capable of disabling the proton beam whenever unacceptable motion of the patient is detected. Preferably, the device should have a fast response time so as to exploit the oscillatory nature of patient motion. In particular, if the motion is attributed to inhalation and exhalation processes, the patient monitoring system should have a response time that is significantly shorter than the breathing period so as to allow the patient to receive safe and effective proton therapy during times of proper alignment between the proton beam and the intended target.

There is also a need for such a devise that is easily adaptable for use in presently available proton beam facilities. For example, it would be advantageous for a medical practitioner to be able to easily move the device from one treatment room to another, quickly mount the device to any available solid structure, and easily and effectively position the device so as to monitor the movement of a patient. Furthermore, the device should be non-invasive to the patient and also provide feedback to the practitioner so as to allow the practitioner to modify the treatment procedure for maximum effectiveness. Moreover, the device should operate reliably and be relatively inexpensive to produce.

SUMMARY OF THE INVENTION

The aforementioned needs are satisfied by the present invention which in one aspect is comprised of a patient motion monitoring system for use with a particle beam therapy system. In this aspect, the system comprises a first energy source adapted to direct a beam towards a surface of the patient substantially positioned in a desired orientation and a first sensor that receive a reflected beam from the first energy source that is reflecting off of the surface of the patient wherein the sensor provides a first signal indicative thereof. The system further comprises at least one positioning mechanism that allows for the first energy source and the first sensor to be positioned a selected distance from the surface of the patient and a controller that receives the first signal from the first sensor and determines the location of the patient based upon the first signal from the sensor, wherein the controller evaluates the first signal to determine if the patient has moved more than a selected threshold amount from the desired orientation.

In another aspect the present invention is comprised of a patient motion monitoring system for use with a particle beam therapy system. In this aspect, the monitoring system comprises a first non-contact sensor that shines a first signal against a surface of a patient substantially positioned in a desired orientation and obtains a reflected signal, wherein the first non-contact sensor provides a first output signal indicative of the received reflected signal and a second non-contact sensor that shines a second signal against a surface of the patient and obtains a reflected signal, wherein the second non-contact sensor provides a second output signal indicative of the received reflected signal. The system also comprises a controller that receives the first and second output signal, wherein the controller uses the first and second output signals to evaluate whether the patient has moved more than a selected threshold amount from the desired orientation and provides a patient movement signal indicative thereof upon determining that the patient has moved more than the selected threshold amount.

In yet another aspect, the present invention is comprised of a particle beam delivery system. The particle beam system comprises a particle beam delivery system for delivering a therapeutic particle beam to a specific location within a patient. The particle beam delivery system further comprises a non-contact patient motion monitoring system, the non-contact patient motion monitoring system having a first non-contact sensor that directs a beam towards a surface of the patient substantially positioned in a desired orientation and receives a reflected beam therefrom, wherein the first non-contact sensor provides a first output signal indicative of the distance of the patient from the first non-contact sensor and wherein the non-contact patient motion monitoring system further includes a controller that receives the first output signal and evaluates the first output signal to determine if the patient has moved more than a selected threshold amount from the desired orientation and wherein the controller provides a patient movement signal adapted to allow for interruption of delivery of the therapeutic particle beam upon determining that the patient has moved more than the selected threshold amount from the desired orientation.

In yet another aspect, the present invention comprises a method of monitoring the motion of a patient. In this aspect, the method comprises directing a first non-contact beam from a first location towards a surface of a patient position substantially in a desired orientation; receiving a reflected beam from the surface of the patient as a result of directing the first non-contact beam towards the surface of the patient; evaluating the reflected beam to determine a distance value that corresponds to the distance of the patient from the first location; determining whether the distance value indicates that the patient has moved more than a selected threshold amount from the desired orientation; and providing a signal indicating that the patient has moved more than the desired threshold amount.

From the foregoing, it will be appreciated that the non contact monitoring system and method of the present invention provides a non-contact system for determining whether the patient has moved from a desired orientation to thereby either provide a warning or inhibit the delivery of therapeutic particle beams. These and other objects and advantages of the present invention will become more fully apparent from the following description taken in conjunction with the accompanying drawings.

DETAILED DESCRIPTION OF THE PREFERRED EMBODIMENT

Figure 1:
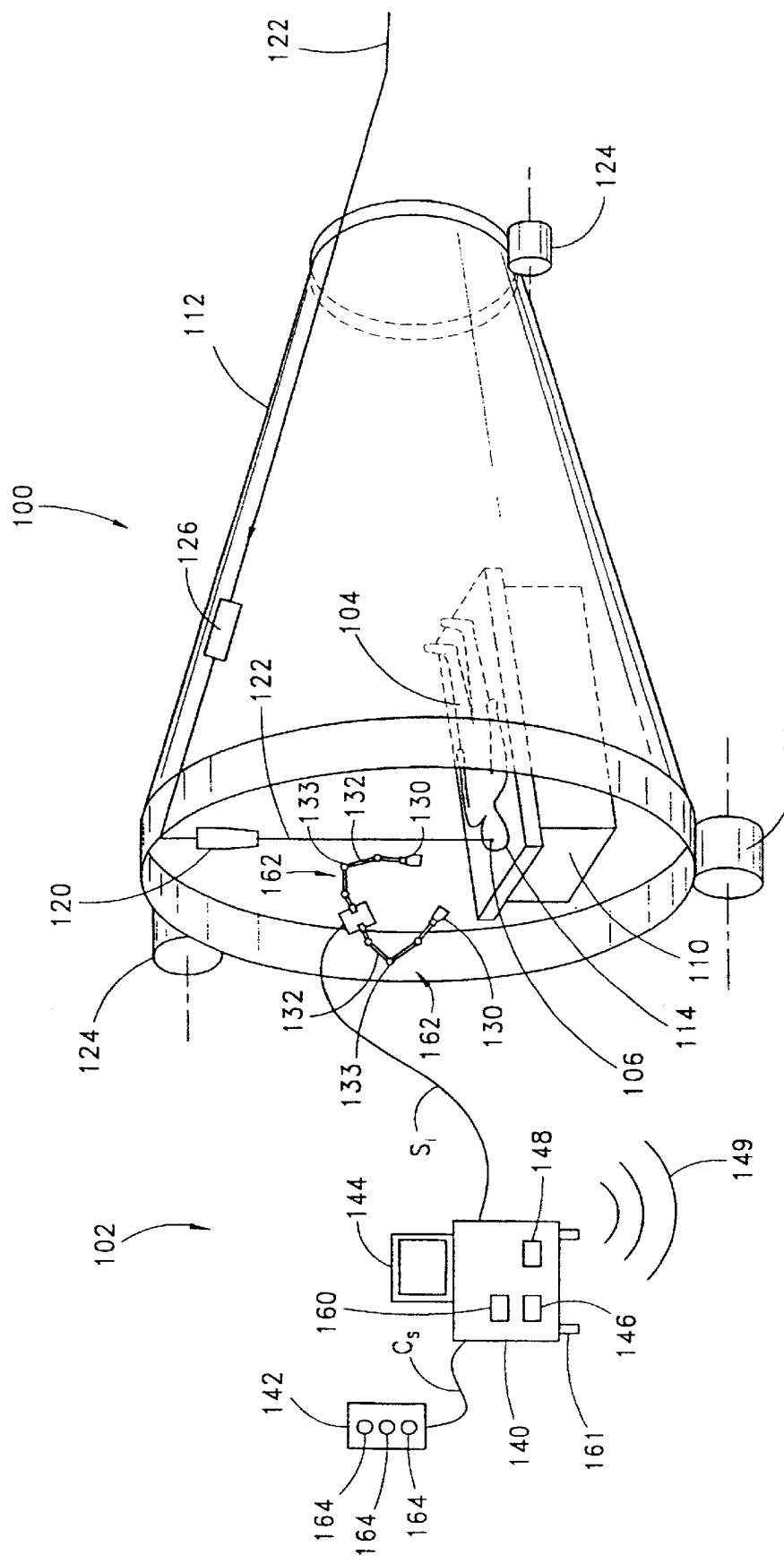
FIG. 1 is a schematic representation of one embodiment of a patient motion monitoring device that operates in conjunction with a proton beam facility.

Reference will now be made to the drawings wherein like numerals referred like parts throughout. FIG. 1 illustrates a patient motion monitoring system 102 configured in accordance with one embodiment of the present invention. In particular, the patient motion monitoring system 102 is designed to operate in conjunction with a therapeutic proton beam facility 100 such as the proton beam facility currently in operation at Loma Linda University Medical Center in Loma Linda, Calif., so as to provide a patient 104 with optimal proton therapy as will be described in further detail below. The proton therapy system 100 is described in greater detail in U.S. Pat. No. 4,870,287 which is hereby incorporated by reference in its entirety. Although this embodiment is described as part of a proton beam facility, it will be appreciated that the patient motion monitoring system 102, in other embodiments, could be adapted to operate in conjunction with other collimated beam devices such as electron beams, lasers, or x-rays.

With reference to FIG. 1, the proton beam facility 100 is comprised of a highly collimated proton beam 122 that is adapted to treat a localized tumor 106 located within the patient 104 who is positioned on a table 110. In this circumstance, the tumor 106 is illustrated in FIG. 1 as being located within the head 114 of the patient 104. However, it will be appreciated that the beam 122 could be used to treat tumors in other regions of the body.

The beam 122 is supplied by a proton accelerator (not shown) with an initial direction that is substantially horizontal. Upon entry into a gantry 112, the beam 122 is deflected by a system of bending magnets 126, shown schematically in FIG. 1, which direct the path of the proton beam 122 along a course that leads to the patient 104. Furthermore, the gantry 112 directs the proton beam 122 through a nozzle 120, located on the circumference of the gantry 112, so as to allow the proton beam 122 to reach the patient 104. In addition, a plurality of rotatable support elements 124 enable the gantry 112 to be rotated with an axis of rotation that is collinear with the initial direction of the beam 122 so as to allow the patient 104 to receive the beam 122 from multiple directions.

While the patient 104 is receiving proton therapy, it is desirable for the energy of the beam 122 to be released within the cellular material of the tumor 106. To accomplish the desired energy transfer, the patient 104 is positioned on the table 110 so that the tumor 106 can be aligned with the beam 122. Furthermore, the beam 122 is directed at a critical portion of the tumor 106 and the energy of the beam 122 is set in accordance with the cellular material that is interposed between the nozzle 120 and the tumor 106. Although it is not illustrated in FIG. 1, the patient 104 is configured with an immobilization device, such as a stereotactic fixation system known in the art, in an attempt to limit the motion of the patient 104.

In an effort to further avoid misalignment between the tumor 106 and the beam 122 due to movement by the patient 104, the patient motion monitoring system 102, shown in FIG. 1, is used in conjunction with the proton beam facility 100. As will be described in greater detail below, the patient motion monitoring system 102 contains a controller 160 that is adapted to produce a plurality of signals that includes a beam interlock signal Bi. In particular, the beam interlock signal Bi is developed by the controller 160 only if the motion of the patient 104 is within threshold limits and the patient motion monitoring system 102 is placed into an armed state. Furthermore, the proton beam facility 100 is adapted to receive the beam interlock signal Bi so as to prevent the beam 122 from reaching the patient 104 unless the beam interlock signal Bi is received by the proton beam facility 100.

The patient motion monitoring system 102 includes a plurality of position detector assemblies 162 with each detector assembly 162 comprised of a position sensor 130 attached to an articulating arm 132 having a plurality of adjustable members 133 so as to allow the position sensor 130 to be positioned near the patient 104. Furthermore, the plurality of position detector assemblies 162 are adapted to develop a corresponding plurality of output position signals Si that are indicative of the position of the patient 104. In one embodiment described below (FIG. 2), the plurality of position detector assemblies 162 is comprised of a first position detector assembly 162a having an output position signal Sa and a second position detector assembly 162b having an output position signal Sb.

As shown in FIG. 1, the plurality of signals Si from the plurality of position detector assemblies 130 are transmitted to a cart 140. As will be described in greater detail below, the cart 140 contains the controller 160 which is adapted to receive and process the signals Si. Furthermore, when the controller 160 is placed in the armed state and the position signals Si remain within an acceptable range, the controller 160 activates the beam interlock signal Bi so as to allow the beam 122 to reach the patient 104. In addition, the controller 160 is adapted to continuously monitors the signals Si so as to allow a practitioner to statistically evaluate the motion of the patient 104. Moreover, if the controller 160 determines that any of the signals Si are beyond acceptable threshold limits, then the controller 160 may activate an audible alarm 148.

As shown in FIG. 1, the patient motion monitoring system 102 further contains a user input device 142 known in the art that is comprised of a plurality of push-buttons 164. In particular, the user may depress the push-buttons 164 so as to generate a plurality of control signals Cs. Furthermore, the controller 160 is adapted to receive the plurality of control signals Cs from the user input device 142 so as to allow the user to manipulate the patient motion monitoring system 102 between the armed state, a standby state, and an alarmed state.

As shown in FIG. 1, the patient motion monitoring system 102 is further comprised of a display 144. Under the direction of the controller 160, the display 144 displays status information regarding the motion of the patient 104. In one embodiment, the controller 160 is adapted to continually update a plurality of status parameters 178 on the display 144 (FIG. 4) that are indicative of the motion of the patient 104. However, in other embodiments, it will be appreciated that the controller 160 could be adapted to generate a plurality of two-dimensional graphs on the display 144 showing the status parameters 178 as functions of time or showing interrelationships among the status parameters 178.

As shown in FIG. 1, the patient motion monitoring system 102 is further comprised of a printer 146. In particular, the printer 146, under the direction of the controller 160, may be used to generate a hard copy of the plurality of status parameters 178.

As shown in FIG. 1, the patient motion monitoring system 102 is further comprised of the audible alarm 148. In particular, the audible alarm 148 is adapted to generate an audible alarm signal 149 under the direction of the controller 160. Furthermore, the controller 160 activates the audible alarm signal 149 whenever the patient motion monitoring system 102 is placed in the armed state and motion of the patient 104 is detected beyond threshold levels.

As shown in FIG. 1, the cart 140 of the patient motion monitoring system 102 is supported on a plurality of wheels 161. In particular, the wheels 161 enable the cart 140 to be quickly and easily moved along a solid surface. Furthermore, the cart 140 is adapted to store the plurality of detector assemblies 162, the controller 160, the user input device 142, the display 144, the printer 146, and the audible alarm 148 so as to allow the patient motion monitoring system 102 to be easily moved from one treatment room to another.

Figure 2:
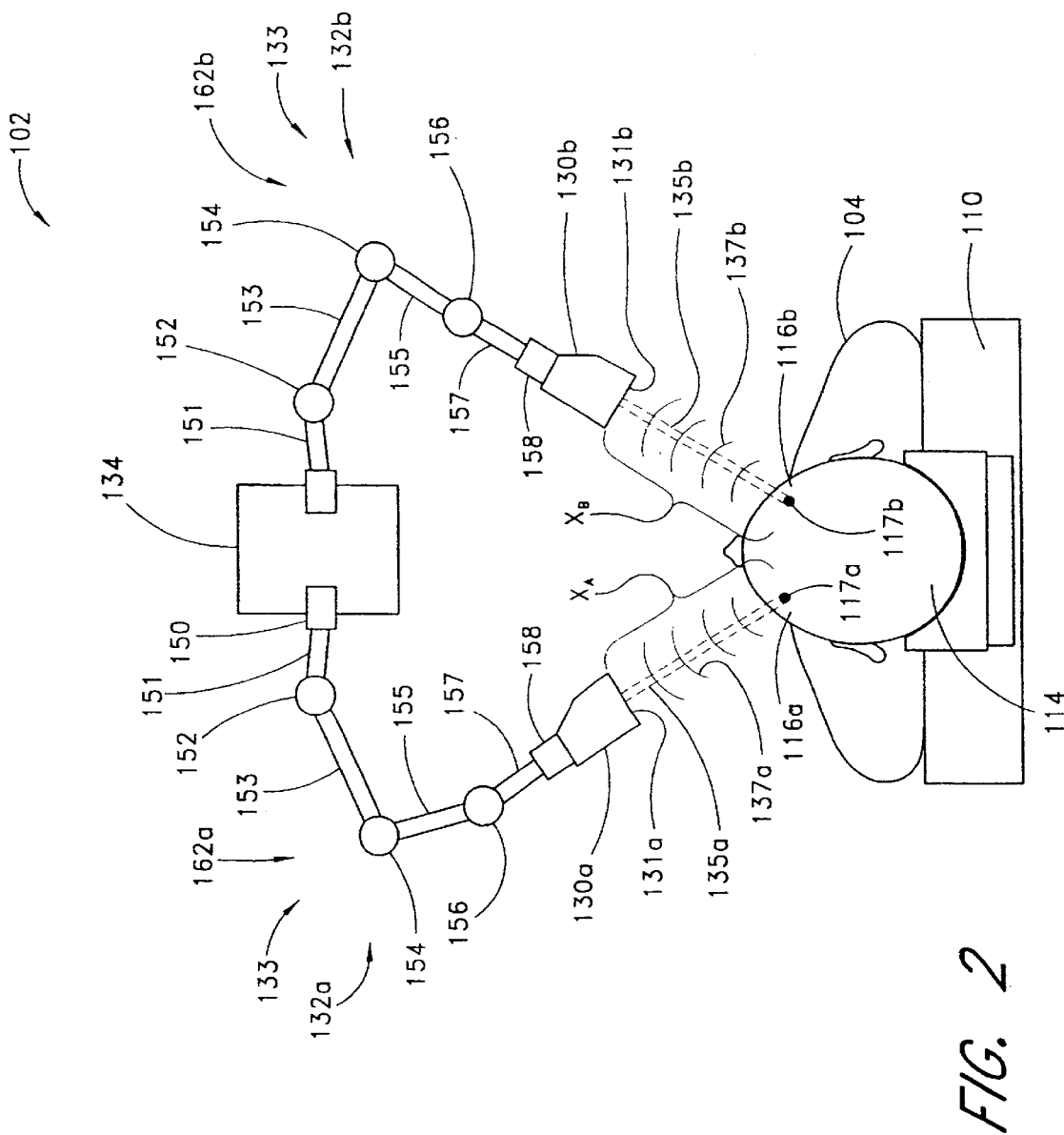
FIG. 2 is a magnified side view of FIG. 1 showing the positioning of the patient motion monitoring device of FIG. 1 with respect to a patient receiving proton therapy.

A magnified side view of one embodiment of the patient motion monitoring system 102 having the first and second position detector assemblies 162a and 162b is shown in FIG. 2. In particular, the patient 104 is shown in a supine position on the treatment table 110 while the patient motion monitoring system 102 detects the motion of the head 114 of the patient 104. In this circumstance, the motion of the head 114 of the patient 104 is monitored by the patient motion monitoring system 102 due to the tumor 106 being located within the head 114 of the patient 104. However, it will be appreciated that the patient motion monitoring system 102 could also be adapted to monitor alternative regions of the patient 104 without departing from the spirit of the present invention.

As will be described in greater detail below, the first position detector assembly 162a is adapted to produce the position signal Sa that is indicative of a distance Xa between a first surface 131a of the position sensor 130a and a first surface 116a of the patient 104. Likewise, the second position detector assembly 162b is adapted to produce the position signal Sb that is indicative of a distance Xb between a first surface 131b of the position sensor 130b and a second surface 116b of the patient 104. Preferably, the first and second position detector assemblies 162a and 162b are arranged so that the distances Xa and Xb are measured along lines that are mutually perpendicular. Furthermore, the position sensors 130a and 130b are designed to measure the distances Xa and Xb provided that Xa and Xb are within an acceptable operating range defined by Xmin and Xmax such that Xmin<Xa<Xmax and Xmin<Xb<Xmax.

In one embodiment, each position sensor 130 of the plurality of position detector assemblies 162 takes the form of an LED displacement sensor. As shown in FIG. 2, the sensor 130a emits a focused beam of light 135a that originates from a non-coherent LED light source contained within the sensor 130a so as to produce a small illuminated circular spot 117a on the first surface 116a of the patient 104 as shown in FIG. 2. Furthermore, the illuminated spot 117a of the first surface 116a substantially behaves like a point source of light with a corresponding diverging pattern of fight 137a that travels back toward the first surface 131a of the sensor 130a. Upon receipt of a portion of the reflected light 137a by the sensor 130a, a positive lens within the sensor 130a refracts the received portion of light 137a so as to form a converging pattern of light (not shown) inside the sensor 130a. Furthermore, the converging pattern of light attempts to converge at a focal plane of the lens to form a focused image of the illuminated spot 117a. Within the sensor 130a, a photodiode array (not shown), which is adapted to generate a signal that corresponds to the size of a circular image formed on the photodiode array, is positioned in the path of the refracted light slightly outside the focal plane of the lens so as to form a substantially circular unfocused real image of the spot 117a on an active region of the photodiode array. In this manner, a calculable relationship is realized between the distance Xa and the diameter of the unfocused image of the spot 117a formed on the photodiode array. Thus, the signal provided by the photodiode array forms the basis for the position signal Sa.

In one embodiment, the second position sensor 130b also takes the form of an LED displacement sensor. In particular, the second position sensor 130b produces the position signal Sb which is indicative of the distance Xb between the first surface 131b of the position sensor 130b and a second surface 116b of the patient 104. As shown in FIG. 2, the position sensor 130b emits a focused beam of light 135b which produces a small illuminated circular spot 117b on the second surface 116b, thus causing a reflected pattern of light 137b having point-like source characteristics. Furthermore, the sensor 130b is adapted with a photodiode array that is positioned in front of a focal plane of a lens so as to develop the signal Sb in a manner that is similar to that of the sensor 130a.

It will be appreciated that LED displacement sensors offers many advantages. In particular, the light produced by LED displacement sensors is harmless both to the patient and the practitioner and therefore does not require additional safety equipment when in use. Furthermore, since LEO displacement sensors measure distance by reflecting light off of a surface, LED displacement sensors do not make direct physical contact with the patient 104. Moreover, LED displacement sensors of the aforementioned type provide a high level of precision and are also capable of making position measurements within a short period of time. As an added benefit, LED displacement sensors are lightweight, robust, and relatively inexpensive to produce.

In one embodiment, each the position sensors 130a and 130b take the form of commercially available LED displacement sensors. In particular, LED displacement sensors manufactured by Omron Electronics Inc. of Japan with model # Z4W-V are utilized. As a result, a position resolution of 10 microns is achieved with a response time of only 5 milliseconds. Furthermore, the operating range of the sensors 130a and 130b varies from Xmin=21 mm up to Xmax 29 mm.

In another embodiment, each position sensor 130 contains an LCD display that indicates the status of the sensor 130. In particular, the LCD display displays a virtual needle that points to a value that corresponds to the measured position Xi. Furthermore, the virtual needle is adapted with a thickness that corresponds to the threshold value Ti.

As depicted in FIG. 2, the articulating arms 132a and 132b of the first and second position detector assemblies 162a and 162b enable the position sensors 130a and 130b to be temporarily positioned so as to monitor the motion of the patient 104. In particular, the plurality of adjustable members 133 of each arm 132 is comprised of a first adjustable member 152, a second adjustable member 154, and a third adjustable member 156 so as to allow each arm 132 to be maneuverable in a manner similar to a human arm as will be described below.

As shown in FIG. 2, each of the articulating arm 132a and 132b are each comprised of a first stud member 151 which is adapted to attach to a first clamp 150 as will be described below. Furthermore, the first stud member 151 is pivotally and rotatably mounted to a first central member 153 by way of the first adjustable member 152. Moreover, the first central member 153 is pivotally mounted to a second central member 155 by way of the second adjustable member 154. Finally, the second central member 155 is pivotally and rotatably mounted to a second stud member 157 by way of the third adjustable member 156, wherein the second stud member 157 is adapted to attach to a second clamp 158.

In one embodiment, each of the articulating arms 132a and 132b take the form of Bogen Magic Arms available from Bogen Arms of Ramsey, N.J. In particular, the Bogen Magic Arm includes the first and third adjustable members 152 and 156 which are both pivotable by 90 degrees and rotatable by 360 degrees. Furthermore, the Bogen Magic Arm includes the second adjustable member 154 that is pivotable by 360 degrees.

As shown in FIG. 2, the first clamp 150 of the first and second position detector assemblies 162a and 162b detachably mounts the first and second position detector assembly 162a 162b to a mounting structure 134. In particular, the first clamp 150 is adapted with locking jaws (not shown) which allows it to detachably mount to the mounting structure 134. In one embodiment, the first clamp 150 is comprised of a Bogen Super Clamp.

As shown in FIG. 2, the second clamp 158 of the first position detector assembly 162a secures the position sensor 130a to the first position detector assembly 162a. In a similar manner, the second clamp 158 of the second position detector assembly 162b secures the position sensors 130b to the second position detector assembly 162. In both cases, the second stud member 157 and the second clamp 158 are adapted to securely attach together. In one embodiment, the second clamp 158 is comprised of a Bogen Super Clamp manufactured by the Manfrotto Corporation.

Advantageously, the position detector assemblies 160 allow for three degrees of movement of the sensors 130a, 130b. Hence, the cart 140 can be positioned adjacent the patient positioned on the treatment table and the position detector assemblies 160 can be adjusted so that the sensors are positioned adjacent the user at the desired distance. Because the assemblies 160a, 160b are independently adjustable, the sensors 130a, 130b and are mounted on a mobile cart, the sensors 130a, 130b can be independently adjusted to accommodate patient's positioned in different locations. Moreover, since the cart 140 is portable, the cart 140 can be positioned adjacent any of a number of different patients positioned at different treatment locations.

Figure 3:
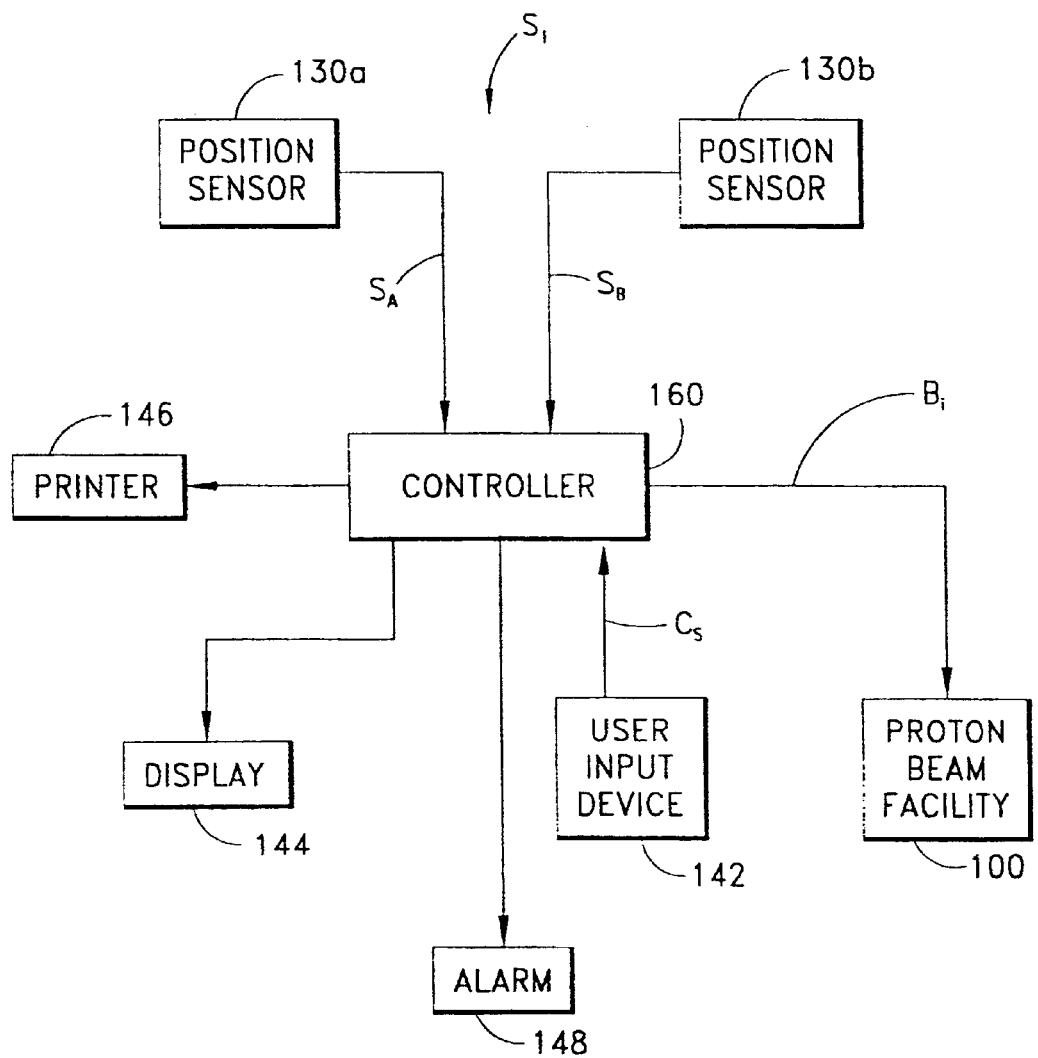
FIG. 3 is a block diagram illustrating some of the components of the patient motion monitoring device of FIG. 1.

A functional block diagram illustrating the electrical components of one embodiment of the patient motion monitoring system 102 is shown in FIG. 3. In particular, the patient motion monitoring system 102 is comprised of the controller 160 which is adapted to receive the position signals Sa and Sb from the position sensors 130a and 130b in a manner known in the art. Furthermore, the controller 160 is associated with a memory 161 that is suitable for storing reference values and accumulating statistical information relating the a proton therapy session.

The controller 160 further includes an arithmetic processing unit known in the art that is capable of performing arithmetic computations. In particular, the controller 160 computes a plurality of patient distances Xi which are based on the plurality of position signals Si received by the controller 160. For example, in the embodiment of FIG. 2, the patient distances Xi are comprised of the distances Xa and Xb which are determined by the signals Sa and Sb respectively. Furthermore, a plurality of reference patient distances XiO are computed based on the state of the position signals Si at the onset of the proton therapy session. Additionally, the controller 160 computes a plurality of patient displacements DXi defined by DXi=Xi–XiO. The controller also compares each of the patient displacements DXi with a corresponding preset threshold value Ti to determine whether the patient has moved significantly. Moreover, the controller 160 iteratively computes a plurality of statistical quantities that relate to the plurality of patient displacements DXi. In one embodiment, the controller 160 takes the form of an Omron Sysmac C200 Programmable Logic Controller manufactured by Omron Electronics Inc. of Japan.

As shown in FIG. 3, the controller 160 of the patient motion monitoring system 102 is adapted to receive user input from the user input device 142 in a manner known in the art. As mentioned previously, the user input device 142 is comprised of the plurality of push-buttons 164. In one embodiment, the push-buttons 164 are comprised of an arm button, a clear alarm button, a threshold button, a disable sensor #2 button, and a research mode button. In particular, the arm button and the clear alarm button allow the patient motion monitoring system 102 to be manipulated between the standby state, the armed state, and the alarm state as will be described more fully below. The threshold button is used to select the threshold values Ti by cycling through possible threshold values. The disable sensor #2 button allows the patient motion monitoring system 102 to operate without the second position detector assembly 162b. The research mode button is used to configure the patient motion monitoring system 102 into a research mode of operation As shown in FIG. 3, the controller 160 of the patient motion monitoring system 102 is also adapted to update the display 144 in a manner known in the art. In one embodiment (FIG. 4), the controller 160 causes the display 144 to display status information regarding the status of the patient motion monitoring system 102 as will be described below. The controller 160 is also adapted to generate output on the printer 146 in a manner known in the art so as to preserve the status information of the patient motion monitoring system 102 in printed form.

As shown in FIG. 3, the controller 160 of the patient motion monitoring system 102 is also adapted to activate the audible alarm 148 in a manner known in the art. In particular, the alarm 148 is activated by the controller 160 when the patient motion monitoring system 102 is configured into the armed mode and any one of the patient displacements components DXi exceed the corresponding thresholds value Ti.

As shown in FIG. 3, the controller 160 of the patient motion monitoring system 102 is also adapted to transmit the beam interlock signal Bi to the proton beam facility 100 in a manner known in the art. In one embodiment, the beam interlock signal Bi is transmitted when the patient motion monitoring system 102 is placed in the armed mode and the patient displacements DXi are within the range of the corresponding thresholds values Ti. Furthermore, the proton beam facility 100 is adapted to produce the proton beam 122 only upon receipt of the beam interlock signal Bi in a manner known in the art.

Figure 4:
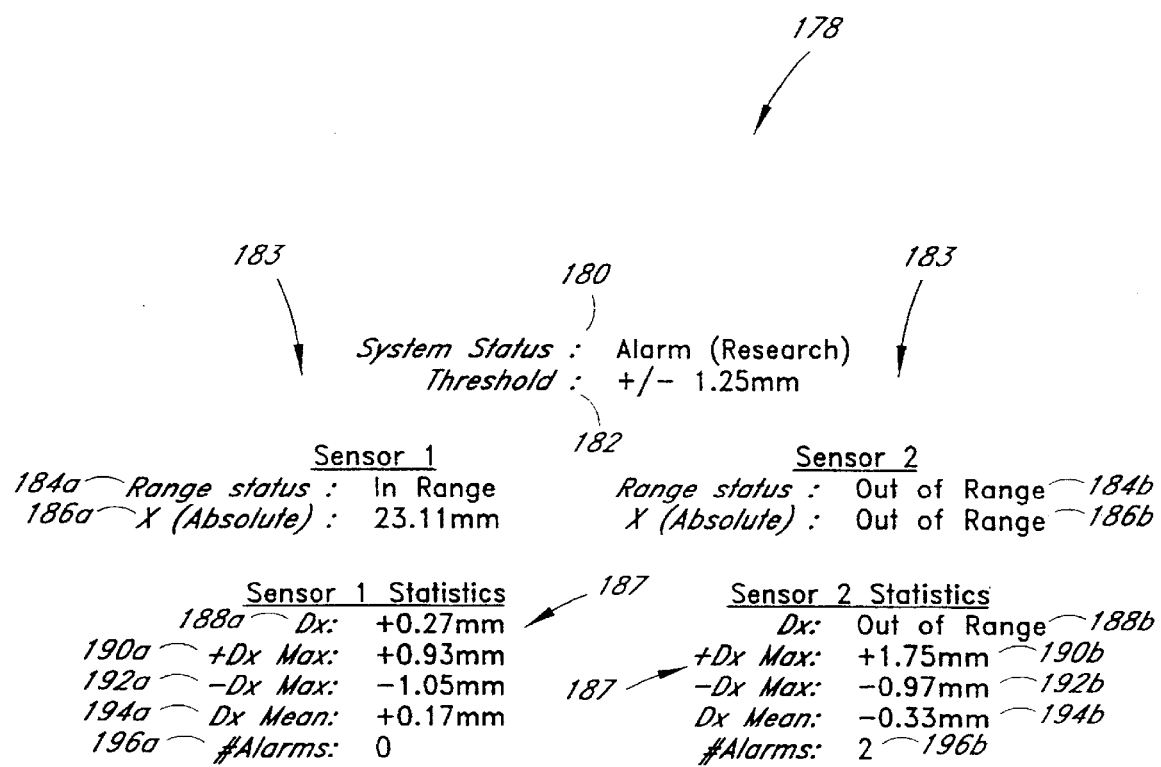
FIG. 4 is a view of a display of the patient motion monitoring device of FIG. 1 which illustrates a sample set of status information that is presented on a display of the device.

Reference will now be made to FIG. 4, which exemplifies the display 144 of one embodiment of the patient motion monitoring system 102. In particular, the plurality of status parameters 178, which are indicative of the operational status of the patient motion monitoring system 102, are displayed on the display 144. Furthermore, the plurality of status parameters 178 includes a plurality of groups 183 each having a plurality of statistical parameters 187, wherein each group 183 represents the status of a corresponding position detector assembly 162

As shown in FIG. 4, the plurality of status parameters 178 includes a system status indicator 180 which indicates the operating mode of the patient motion monitoring system 102. In particular, the system status indicator 180 indicates that the patient motion monitoring system 102 is either in the standby state, the armed state, or the alarmed state. Furthermore, the system status indicator 180 indicates whether the controller 160 is operating in a research mode.

As shown in FIG. 4, the status parameters 178 includes a threshold indicator 182. In particular, the threshold indicator 182 corresponds to the current threshold values Ti utilized by the controller 160 for determining whether significant motion of the patient 104 has occurred. In the embodiment of FIG. 4, each of the threshold values Ti are identical to each other. However, in other embodiments, it will be appreciated that the threshold values Ti could be set independently of each other and displayed on the display 144 in an independent manner.

As shown in FIG. 4, the plurality of status parameters 178 includes the plurality of groups 183, wherein each group 183 signifies the operational status a corresponding position detector assembly 162. In particular, the group 183 on the left side of the display corresponds to the status of the first detector assembly 162a and the group 183 on the right side of the display corresponds to the status of the second detector assembly 162b.

Each group 183 of the plurality of status parameters 178 includes a range status indicator 184 which can either be In Range, Out of Range, or Disabled. When the patient motion monitoring system 102 is placed in the standby state, if the range status indicator 184 is In Range, then the controller 160 has determined that the patient 104 is within the operating range of the corresponding position detector assembly 162 defined by Xi+Ti<Xmax and Xi−Ti>Xmin. Correspondingly, when the 102 is placed in the standby state, if the range status indicator 184 is Out of Range, then the controller 160 has determined that the patient 104 is not within the operating range of the corresponding position detector assembly 162 defined by Xi+Ti>Xmax or Xi−Ti<Xmin. However, when the patient motion monitoring system 102 is in either the armed state or the alarmed state, if the range status indicator 184 is In Range, then the controller 160 has determined that the patient 104 is within the threshold range of the corresponding position detector assembly 162 defined by −Ti<DXi<Ti. Otherwise, when the patient motion monitoring system 102 is in either the armed state or the alarmed state, if the range status indicator 184 is Out of Range, then the controller 160 has determined that the patient 104 is not within the threshold range of the corresponding position detector assembly 162 defined by DXi>Ti or DXi<−Ti.

It is also possible for the range status indicator 184 on the left side of the display 144 corresponding to the second position detector assembly 162b to display the word Disabled. If this is the case, then the user has previously opted to disable the second detector assembly 162b by way of the disable sensor #2 button of the user input device 142 so as to cause the controller 160 to ignore the position signal Sb when determining whether to generate the beam interlock signal Bi.

Each group 183 of the plurality of status parameters 178 also includes an Xi indicator 186. In particular, the Xi indicator 186 corresponds to the most recently recorded patient distance Xi and is updated during all operating states of the patient motion monitoring system 102. Furthermore, if the second position detector assembly 162b is disabled, then the corresponding Xi indicator 186 displays the word Disabled.

Each group 183 of the plurality of status parameters 178 also includes a DXi indicator 188. In particular, the DXi indicator 188 corresponds to the most recently computed value of DXi and is updated during all operating states of the patient motion monitoring system 102. Furthermore, if the second position detector assembly 162b is disabled, then the corresponding DXi indicator 188 displays the word Disabled. Moreover, if the patient is outside of the operational range of the corresponding sensor 130, then the DXi indicator 188 displays the phrase Out of Range Each group 183 of the plurality of status parameters 178 also includes a +DXi max indicator 190. In particular, the +DXi max indicator 190 corresponds to the largest positive value of DXi computed during the treatment session and is only updated during the armed state. Furthermore, the +DXi max indicator 190 is cleared to a value of 0.0 upon startup and upon a transition between the armed state and the standby state. However, the +DXi max indicator 190 is preserved upon a transition between the alarmed state and the standby state.

Each group 183 of the plurality of status parameters 178 also includes a −DXi max indicator 192. In particular, the −DXi max indicator 192 corresponds to the largest negative value of DXi computed during the treatment session and is only updated during the armed state. Furthermore, the −DXi max indicator 192 is cleared to a value of 0.0 upon startup and upon a transition between the armed state and the standby state. However, the −DXi max indicator 192 is preserved upon a transition between the alarmed state and the standby state.

Each group 183 of the plurality of status parameters 178 also includes a DXi mean indicator 194. In particular, the DXi mean indicator 194 corresponds to average of all value of DXi computed during the treatment session and is only updated during the armed state. Furthermore, the DXi mean indicator 194 is cleared to a value of 0.0 upon startup and upon a transition between the armed state and the standby state. However, the DXi mean indicator 194 is preserved upon a transition between the alarmed state and the standby state.

Each group 183 of the plurality of status parameters 178 also includes a number of alarms indicator 196. In particular, the number of alarms indicator 196 corresponds to the number of direct transitions that have occurred between the armed state and the alarmed state as a result of the corresponding position detector assembly 162 detecting above threshold movement of the patient 104. Upon a transition from the standby state to the armed state, the number of alarms indicator 196 is reset to zero. Furthermore, if the second position detector assembly 162b is disabled, then the corresponding number of alarms indicator 196 displays the word Disabled.

Figure 5A:
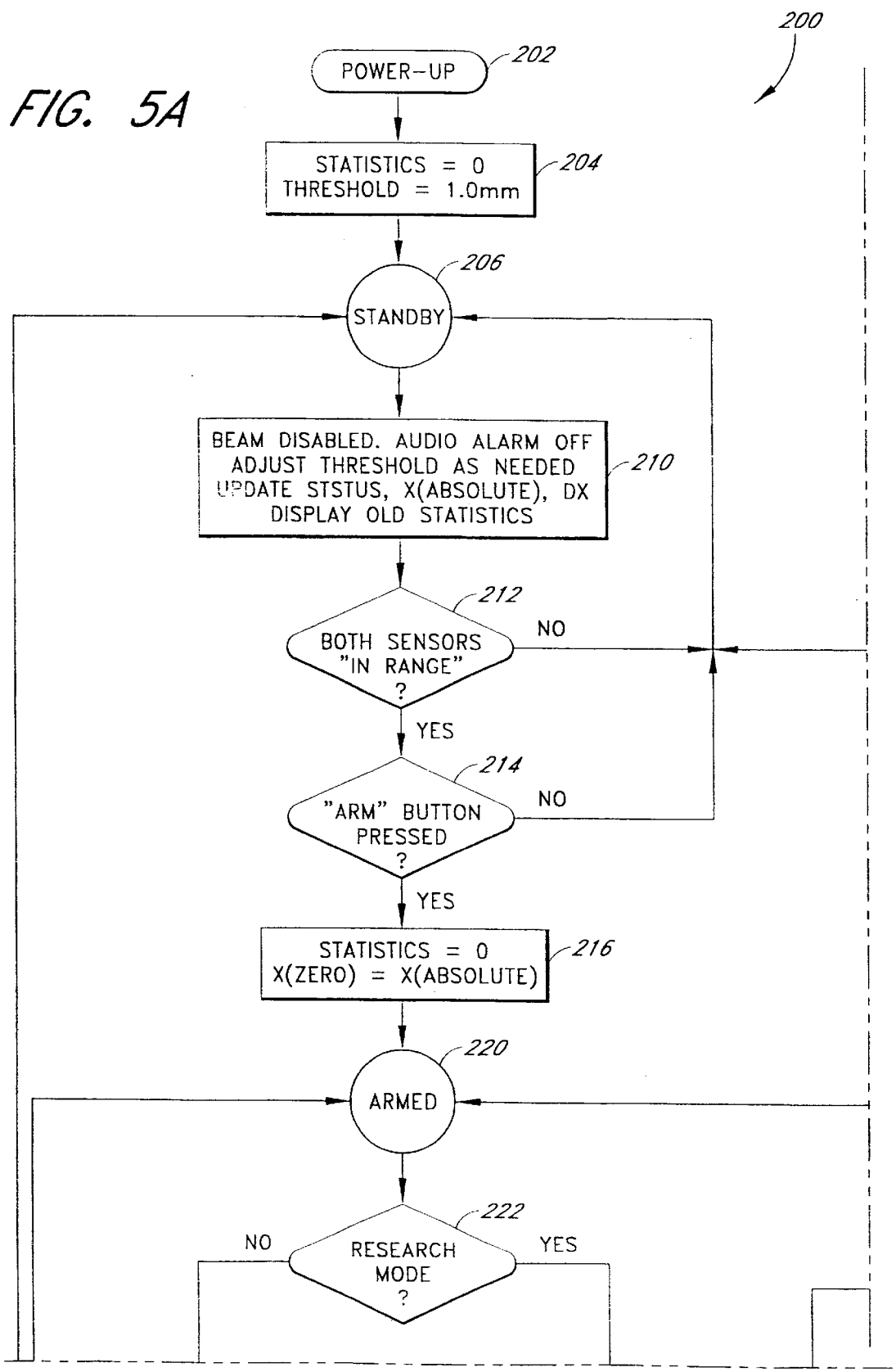
FIG. 5 is a flow chart which illustrates the operation of the patient motion monitoring device of FIG. 1.
Figure 5B:
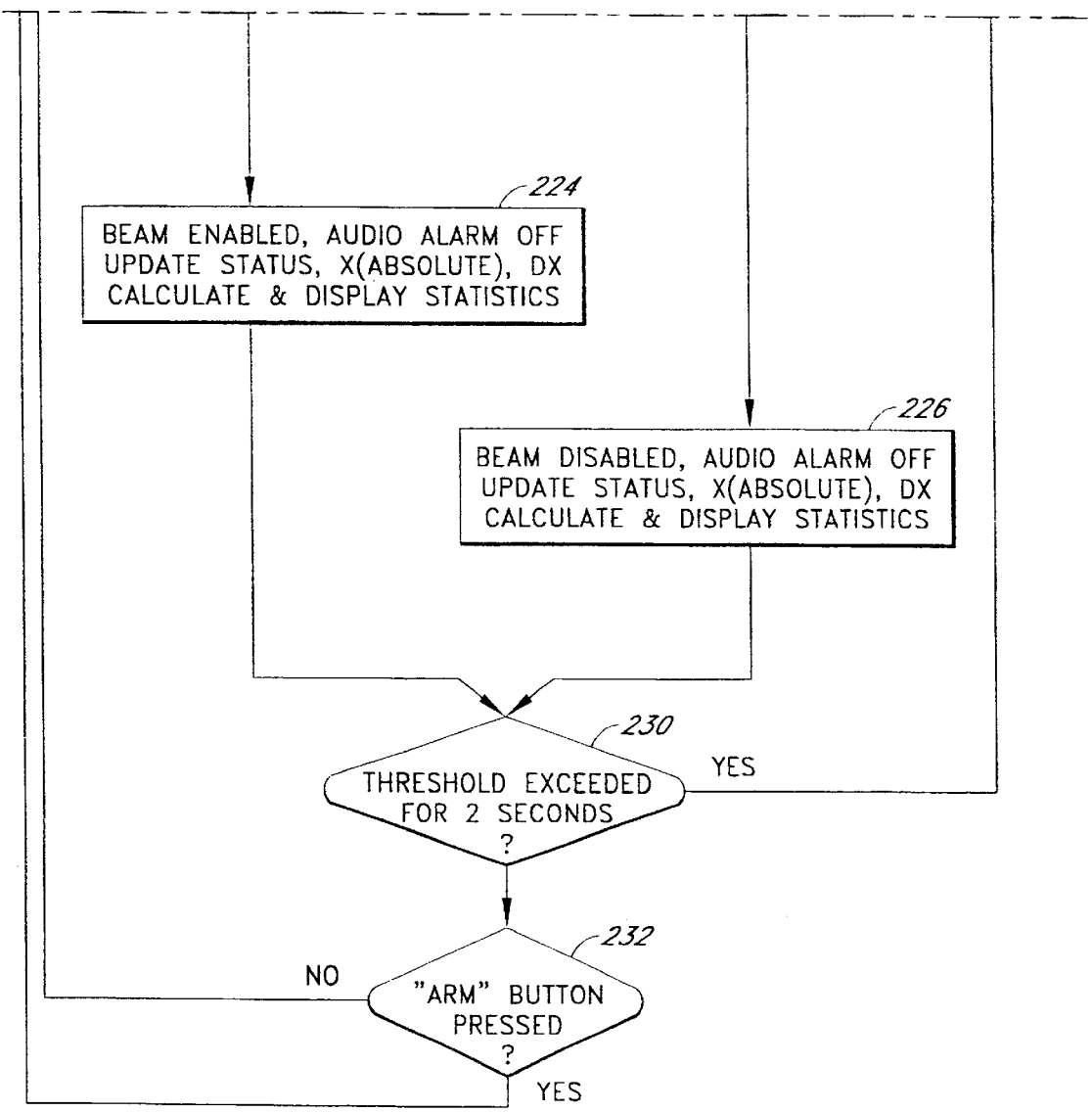
Figure 5C:
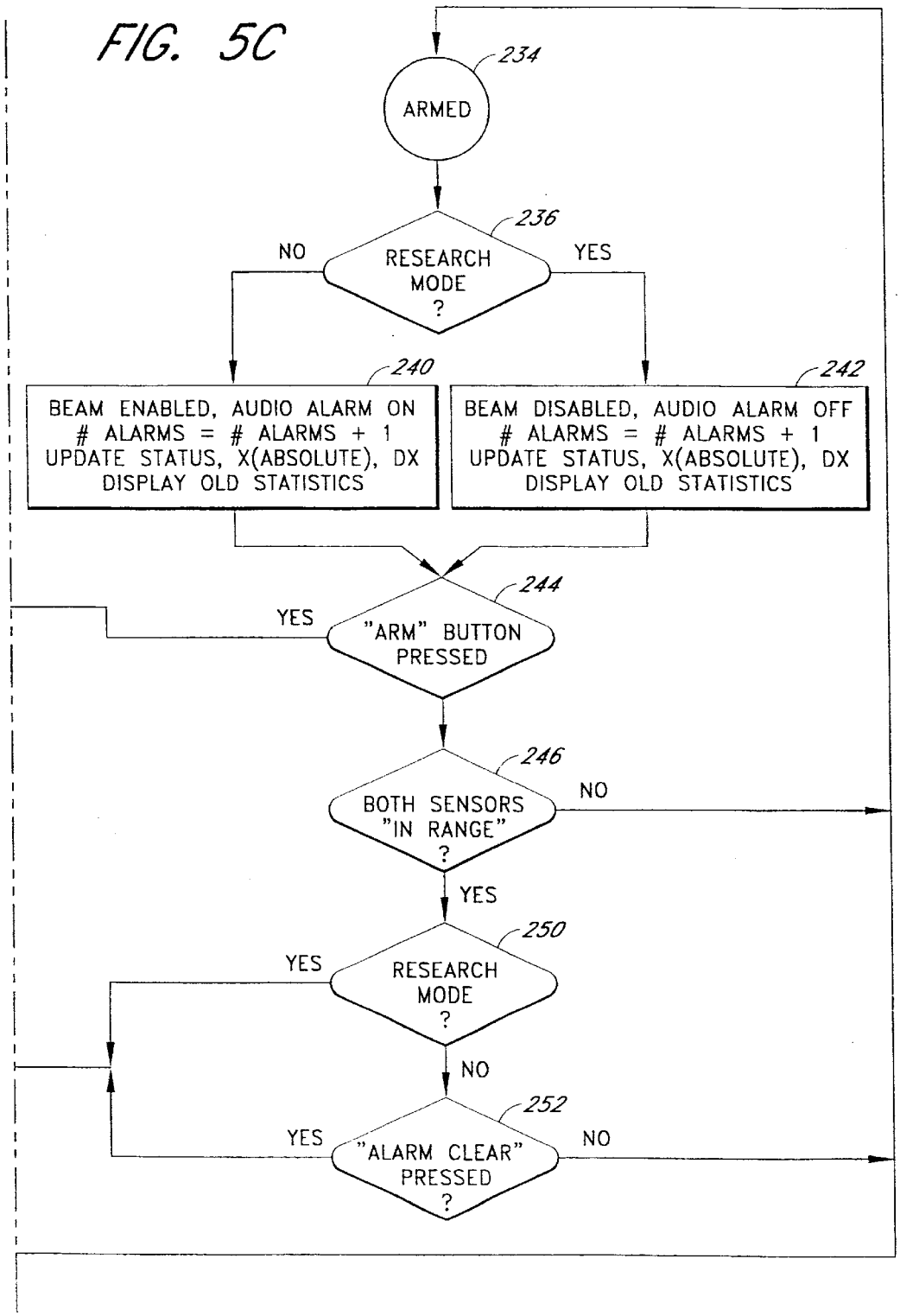

Reference will now be made to FIG. 5, which illustrates a flow chart 200 that describes the operation of one embodiment of the controller 160 of the patient motion monitoring system 102. In particular, the user can manipulate the controller 160 between a standby state 206, an armed state 234, and an alarmed state 220. Furthermore, the user may initiate a research mode of operation as will be described below.

Following a power-up state 202, the controller 160, in a state 204, resets all statistical quantities and initially sets all threshold values Ti to 1 mm. As will be described below, the statistical quantities are updated and displayed by the controller 160 on the display 144 during subsequent operation of the controller 160. Furthermore, the threshold values Ti can be manually set during subsequent operation of the controller 160.

The controller 160 then continues into a standby state 206 so as to allow a user to position the sensors 130a and 130b first and second position detectors 162a and 162b within the operating range of the patient 104. As discussed above, the sensors 130a, 130b are preferably positioned a distance that is within the operating range. Preferably, the controller 160 provides visual feedback signals on the display 144 (FIG. 2) which allows the user to correctly position the sensors. The controller 160, in a state 210, then resets the audio alarm and monitors the threshold button of the user input device 142 so as to allow the user to change the threshold values Ti. In this way, the user can set a value which will result in the system giving a signal indicating that the patient has moved beyond a desired threshold. The controller 160 then updates the display 144 with the current plurality of status parameters 178.

The controller then monitors the position signals Sa and Sb, in a decision state 212, to determine whether the patient 104 is within the operational range of the position sensors 130a and 130b. If the patient is not within the operational range of the position sensors 130a and 130b, then the controller 160 returns the standby state 206.

If the controller 160 determines that the patient 104 is within the operational range of the position sensors 130a and 130b, then the controller 160 proceeds to monitor the action of the arm button of the user input device 142 in the decision state 214. If the controller 160 determines that the arm button has not been activated, then the controller 160 returns to the standby state 206.

If the controller 160 determines, in the decision state 214, that the arm button has been pressed, then all statistical quantities are reset in a state 216. The system 102 is now armed and ready to detect patient movement and provide a signal when this movement exceeds the threshold values set in state 204. Furthermore, the position signals Sa and Sb are read and evaluated by the controller 160 and used to compute new position reference values XiO having components XaO and XbO. From there, the controller enters an armed state 220. While in the armed state 220, the controller 160 monitors the research mode button of the user input device 142 to determine whether a research mode of operation is requested by the user. As discussed above, the patient monitoring system can either be used to monitor patient movement for treatment or it can be used to obtain research information about a patient's movement.

If the controller 160 determines that the research mode button has not been activated in the decision state 222, then the controller 160, in a state 224, generates the beam interlock signal Bi so as to allow the proton beam 122 to reach the patient 104. Furthermore, the audio alarm is deactivated, new values of Xi having components Xa and Xb are computed based on the received position signals Sa and Sb, new patient displacements DXi having components DXa=Xa−XaO and DXb=Xb−XbO are computed, the new patient displacements DXi are folded into the plurality of status parameters 178, and the display 144 is updated so as to include the newly computed values of Xi and DXi.

If the controller 160 determines, in the state 222, that the research mode button has been activated, then the controller 160, in a state 226, does not activate the beam interlock signal Bi so as to prevent the proton beam 122 from exiting the nozzle 120. Furthermore, the audio alarm is deactivated, new values of Xi are computed based on the received position signals Si, new patient displacements DXi having components DXa=Xa−XaO and DXb=Xb−XbO are computed, the patient displacements DXi are folded into the statistical information, and the display 144 is updated so as to include the newly computed values of Xi and DXi.

As shown in FIG. 5, the controller continues into a decision state 230 whereby the patient displacements DXi are compared with the threshold values Ti. In particular, if the controller 160 determines that all of the patient displacements DXi have not exceeded the threshold values Ti for a period of time that exceeds 2 seconds, then the controller 160 monitors the arm button of the user input device 142 in a decision state 232.

If the controller 160, in the decision state 232, detects that the arm button has been activated, then the controller 160 returns to the standby state 206 so as to allow the patient 104 to be safely repositioned. Otherwise, the controller 160 reenters the armed state 220 so as to allow the patient 104 to continue receiving proton therapy.

However, if the controller 160, in the state 230, determines that one or more of the patient displacements DXi have exceeded the threshold values Ti for a period of time that exceeds 2 seconds, then the controller enters an alarmed state 234. If this situation occurs, then significant motion of the patient 104 has been detected by the controller 160.

The controller 160 then continues into a decision state 236 whereby the controller 160 determines whether the research mode is requested the controller 160 determines that the research mode is not requested, then the controller 160, in a state 240, deactivates the beam interlock signal Bi so as to prevent the proton beam 122 from reaching the patient 104. The controller 160 then activates the audio alarm 148 and increases an alarm counter by one. The controller 160 then updates the display 144 with the current plurality of status parameters 178.

If the controller 160, in the decision state 236, determines that the research mode is requested, then the controller 160, in a state 242, deactivates the beam interlock signal Bi so as to prevent the proton beam 122 from reaching the patient 104. The controller 160 then increases an alarm counter by one and updates the display 144 with the current plurality of status parameters 178.

The controller 160, in a decision state 244, then monitors the action of the arm button of the user input device 142. If the controller 160 detects that the arm button has been activated, then the controller 160 returns to the standby state 206. However, if the controller 160 determines that the arm button has not been pressed, then the controller 160 proceeds to monitor the position signals Si in a decision state 246 so that new patient displacements DXi can be computed by the controller 160. If the new patient displacements DXi are not within range of the threshold values Ti, then the controller 160 returns to the alarmed state 234.

If the new patient displacements DXi are within range of the threshold values Ti, then the controller 160 continues into a decision state 250 whereby the controller 160 determines whether the research mode is requested. If the controller 160 determines that the research mode is requested, then the controller returns to the standby state.

If the controller determines that the research mode is not requested in the decision state 250, then the controller 160 monitors the clear alarm button in a decision state 252. If the controller 160 detects the activation of the clear alarm button, then controller 160 returns to the standby state 206. Otherwise, the controller returns to the alarmed state 234.

It will be appreciated that the a patient motion monitoring system 102 described above is capable of continually detecting the position of the patient 104 during a proton therapy session. In particular, the patient motion monitoring system 102 includes the plurality of position detector assemblies 162 which are adapted to generate the plurality of position signals Si that are indicative of the position of the patient 104. The position signals Si are received by the controller 160 of the patient motion monitoring system 102 to obtain the measured positions Xi. The controller 160 also compares the measured positions Xi with reference positions XiO to determine the patient displacements DXi. If the patient displacements DXi are outside the range of the threshold values Ti, then above threshold movement of the patient 104 is detected by the controller 160 of the patient motion monitoring system 102.

While the patient motion monitoring system 102 is placed in the armed state and the detected position of the patient does not change beyond the threshold value Ti, the beam interlock signal Bi is activated by the patient motion monitoring system 102 so that the patient 104 can receive treatment. However, if the detected position of the patient changes beyond the threshold value Ti, then the patient motion monitoring system 102 deactivates the beam interlock signal Bi so as to prevent the proton beam 122 from damaging healthy tissue of the patient 104. Furthermore, when above threshold movement is detected by the patient motion monitoring system 102, the audible alarm 148 is activated. Moreover, the status parameters 178 are continually updated and displayed on the display 144 so as to inform a user of the degree of movement of the patient 104.

As shown in the flow chart of FIG. 5, the system can either be configured to control the delivery of treatment beams to the patient or it can also be used to obtain information about the movement of the patient. It will be appreciated that the efficacy of different patient immobilization systems can be evaluated by determining the amount of motion using the patient monitoring system of the present invention.

It will also be appreciated that the patient motion monitoring system 102 is both portable and easy to setup. In particular, the mobile cart 140 of the patient motion monitoring system 102 is adapted to store all of the components of the patient motion monitoring system 102. Furthermore, the clamp 150 of each position detector assembly 162 is adapted to quickly and easily attach to the mounting surface 134 so as to mechanically support the position detector assemblies 162. Moreover, the plurality of adjustable members 133 of each position detector assembly 162 enable the sensors 130 to be conveniently placed within operating range of the patient 104.

It will also be appreciated that the position sensors 130 of the patient motion monitoring system 102 operate without physically contacting the patient. In particular, non-hazardous visible light is emitted by each position sensor 130 so as to create an illuminated spot on the skin of patient 104. The reflected light from the illuminated spot is received by the sensor 130 so as to generate the corresponding position signal Si. Furthermore, the position detection method does not require the patient 104 to wear any kind of position detecting apparatus. Moreover, the position sensors 130 generate the position signals Si with a position resolution of 10 microns and a response time of 5 milliseconds.

Although the preferred embodiment of the present invention has shown, described and pointed out the fundamental novel features of the invention as applied to this embodiment, it will be understood that various omissions, substitutions and changes in the form of the detail of the device illustrated may be made by those skilled in the art without departing from the spirit of the present invention. Consequently, the scope of the invention should not be limited to the foregoing description, but should be defined by the appending claims.

What is claimed is:

1. A patient motion monitoring system for use with a particle beam therapy system, the system comprising:
    a first energy source adapted to direct energy towards a surface of a patient substantially positioned in a desired orientation;
    a first sensor that receives reflected energy from the first energy source that is reflecting off of the surface of the patient wherein the sensor provides a first signal indicative thereof;
    at least one positioning mechanism that allows for the first energy source and the first sensor to be positioned at a selected distance from the surface of the patient;
    a controller that receives the first signal from the first sensor and determines the location of the patient based upon the first signal from the sensor, wherein the controller evaluates the first signal to determine if the patient has moved more than a selected threshold amount from the desired orientation.

2. The system of claim 1, further comprising a second energy source adapted to direct energy towards a surface of the patient positioned in a desired orientation and a second sensor that receives reflected energy from the second energy source that is reflecting off of the surface of the patient.

3. The system of claim 2, wherein the controller receives a second signal from the second sensor and determines a location of the patient with respect to the second sensor based upon the signal from the second sensor and wherein the controller evaluates the second signal in conjunction with evaluating the first signal to determine if the patient has moved more than the selected threshold amount from the desired orientation.

4. The system of claim 1, wherein the controller produces a signal indicative of when the patient has moved more than the selected threshold amount from the desired orientation.

5. The system of claim 4, wherein the signal produced by the controller is an alarm signal that signifies to a user that the patient has moved more than the selected threshold amount from the desired orientation.

6. The system of claim 4, wherein the signal produced by the controller is a beam signal that can be used by a particle beam control system to interrupt the delivery of a therapeutic beam to the patient.

7. The system of claim 4, wherein the controller records a degree of movement of the patient.

8. The system of claim 4, wherein the controller produces the signal only when the first signal indicates that the patient has moved more than the selected threshold amount for a pre-selected time period to allow the patient to return to the desired orientation.

9. The system of claim 8, wherein the first signal is accurate to within 10 microns of the location of the patient from the sensor.

10. The system of claim 9, wherein the controller is configured to allow the user to set the selected threshold amount.

11. The system of claim 10, wherein the user can select a selected threshold amount of 1 mm movement in a distance from the first sensor such that the patient is no longer in the desired orientation.

12. The system of claim 1, wherein the first energy source is comprised of an LED and the first sensor is comprised of an LED receiver that receives the light reflected off of the surface of the patient and evaluates the received light to produce the first signal.

13. The system of claim 1, wherein the at least one positioning assembly is comprised of a base and a positioning assembly that is mounted thereto which has three degrees of movement to facilitate positioning of the first energy source and the first sensor at a desired distance from the patient and in a desired orientation.

14. The system of claim 13, further comprising a mobile cart containing the base and the controller so that the base and controller can be used in conjunction with a plurality of different treatment locations in a particle beam treatment system and wherein the controller can be communicatively linked to a control system for the particle beam treatment system.

15. A patient motion monitoring system for use with a particle beam therapy system the monitoring system comprising:
    a first non-contact sensor that shines a first signal against a first surface of a patient substantially positioned in a desired orientation and obtains a reflected signal, wherein the first non-contact sensor provides a first output signal indicative of the distance between the first sensor and the first surface;
    a second non-contact sensor that shines a second signal against a second surface of the patient and obtains a reflected signal, wherein the second non-contact sensor provides a second output signal indicative of the distance between the second sensor and the second surface;
    a controller that receives the first and second output signal, wherein the controller uses the first and second output signals to evaluate whether the patient has moved more than a selected threshold amount from the desired location and provides a patient movement signal indicative thereof upon determining that the patient has moved more than the selected threshold amount.

16. The system of claim 15, wherein the first non-contact sensor and the second non-contact sensor are positionable so that the first and second non-contact sensors can be positioned with respect to the patient so that the first and second output signals provide an indication of the amount the patient has moved along an axes corresponding to the first and second signals of the first and second non-contact sensors.

17. The system of claim 16, further comprising first and second positioning assemblies having multiple degrees of motion upon which the first and second non-contact sensors are respectively mounted so that the first and second non-contact sensors can be positioned with respect to the patient at a selected distance from the surfaces of the patient.

18. The system of claim 15, wherein the controller receives the first and second output signals which are indicative of the distance of the patient from the first and second non-contact sensors and wherein the controller uses the first and second output signals to calculate the movement of the patient from the desired orientation.

19. The system of claim 15, wherein the first and second non-contact sensors are LED sensors which direct a light beam along an axis towards the patient and measure the returning light to obtain an indication of the distance of the surface of the patient from the sensor.

20. The system of claim 19, wherein the first and second non-contact sensors provide a signal indicative of the distance of the patient from the first and second non-contact sensors to within a tolerance of approximately 10 microns.

21. The system of claim 20, wherein the controller is configured to allow the user to set the selected threshold amount.

22. The system of claim 21 wherein the controller is configured to allow the user to set the selected threshold amount to 1 mm such that the controller produces the patient movement signal when the patient has moved more than 1 mm from the desired orientation.

23. The system of claim 15, wherein the patient movement signal produced by the controller is an alarm signal that signifies to a user that the patient has moved more than the selected threshold amount from the desired orientation.

24. The system of claim 15, wherein the patient movement signal produced by the controller is a beam signal that can be used by a particle beam control system to interrupt the delivery of a therapeutic beam to the patient.

25. The system of claim 15, wherein the controller records a degree of movement of the patient.

26. The system of claim 15, wherein the controller produces the patient movement signal only when the first and second output signals indicates that the patient has moved more than the selected threshold amount for a pre-selected time period to allow the patient to return to the desired orientation.

27. A particle beam delivery system comprising:
a particle beam delivery system for delivering a therapeutic particle beam to a targeted region within a patient; and
a non-contact patient motion monitoring system having a first non-contact sensor that directs a beam towards a first surface of the patient positioned so that the first surface is disposed at a desired location and receives a reflected beam therefrom, wherein the first non-contact sensor provides a first output signal indicative of the distance of the first surface from the first non-contact sensor and wherein the non-contact patient motion monitoring system further includes a controller that receives the first output signal and evaluates the first output signal to determine if the first surface of the patient has moved more than a selected threshold amount from the desired location and wherein the controller provides a patient movement signal adapted to allow for interruption of delivery of the therapeutic particle beam upon determining that the first surface of the patient has moved more than the selected threshold amount from the desired location.

28. The system of claim 27, wherein the non-contact patient motion monitoring system further comprises a second non-contact sensor that directs a beam to a second surface of the patient and receives a reflected beam therefrom, wherein the second non-contact sensor provides a second output signal indicative of the distance between the second surface of the patient from the second non-contact sensor.

29. The system of claim 28, wherein the controller evaluates both the first output signal and the second output signal to determine if the patient has moved more than a selected threshold amount from the desired orientation.

30. The system of claim 27, wherein the first non-contact sensor and the second non-contact sensor are positionable so that the first and second non-contact sensors can be positioned with respect to the patient so that the first and second output signals provide an indication of the amount of the patient has moved along an axes corresponding to the first and second signals of the first and second non-contact sensors.

31. The system of claim 30, further comprising first and second positioning assemblies having multiple degrees of motion upon which the first and second non-contact sensors are respectively mounted so that the first and second non-contact sensors can be positioned with respect to the patient at a selected distance and in selected directions from the surfaces of the patient.

32. The system of claim 27, wherein the first and second non-contact sensors are LED sensors which direct a light beam along an axis towards the patient and measure the returning light to obtain an indication of the distance of the surface of the patient from the first and second non-contact sensors.

33. The system of claim 32, wherein the first and second non-contact sensors provide a signal indicative of the distance of the patient from the first and second non-contact sensors to within a tolerance of approximately 10 microns.

34. The system of claim 27, wherein the controller is configured to allow the user to set the selected threshold amount.

35. The system of claim 34, wherein the controller is configured to allow the user to set the selected threshold amount to 1 mm such that the controller produces the patient movement signal when the patient has moved more than 1 mm in a direction defined either by the first or second non-contact sensors from the desired orientation.

36. The system of claim 35, wherein the controller records a degree of movement of the patient.

37. The system of claim 27, wherein the controller produces the patient movement signal only when the first and second output signals indicates that the patient has moved more than the selected threshold amount for a pre-selected time period to allow the patient to return to the desired orientation.

38. A method of monitoring a position of a patient, the method comprising:
directing a first non-contact beam from a first location towards a first surface of a the patient;
receiving a first reflected beam from the first surface of the patient;
evaluating the first reflected beam to measure a first distance between the first surface and the first location; and
providing a signal when the first measured distance is greater than a first threshold value.

39. The method of claim 38, wherein directing a first non-contact beam from a first location towards a first surface of the patient comprises directing a beam from a first LED sensor device that is mounted on a support assembly that is positionable and positioning the first LED sensor in a position so that movement of the patient in a direction along the beam of the first LED sensor results in a change in the measured first distance.

40. The method of claim 39, wherein evaluating the first reflected beam comprises evaluating the size of the first reflected beam to obtain a signal indicative of the distance between the first surface of the patient and the first location.

41. The method of claim 38, further comprising:
directing a second non-contact beam from a second location towards a second surface of the patient;
receiving a second reflected beam from the second surface of the patient; and
evaluating the second reflected beam to measure a second distance between the second surface of the patient and the second location.

42. The method of claim 41, wherein said providing a signal further comprises providing the signal when the second measured distance is greater than a second threshold value.

43. The method of claim 42, wherein the first and second threshold values are approximately equal to 1 mm.

44. The method of claim 38, wherein said providing a signal further comprises providing a signal only if the first measured distance is greater than the first threshold value for a pre-selected period of time to permit the first surface of the patient to return to a desired location.

45. The method of claim 44, wherein the pre-selected time period is approximately 2 seconds.

46. The method of claim 45, wherein the signal is adapted to allow for interruption of delivery of a therapeutic particle beam to the patient.

47. The method of claim 44, wherein the signal is adapted to warn a user that the location of the patient is outside of an acceptable range.

* * * * *